(12) United States Patent
Kim et al.

(10) Patent No.: US 8,605,937 B2
(45) Date of Patent: Dec. 10, 2013

(54) METHOD OF ADJUSTING BRIGHTNESS OF ILLUMINATION DEVICE AND BIO DISK DRIVE USING THE METHOD

(75) Inventors: Jong-cheol Kim, Seoul (KR); Chung-ung Kim, Yongin-si (KR); Ki-ju Lee, Suwon-si (KR); Jong-jin Park, Yongin-si (KR); Dong-hwi Cho, Suwon-si (KR); Su-bong Bae, Suwon-si (KR)

(73) Assignee: Samsung Electronics Co., Ltd., Suwon (KR)

( * ) Notice: Subject to any disclaimer, the term of this patent is extended or adjusted under 35 U.S.C. 154(b) by 796 days.

(21) Appl. No.: 12/731,244

(22) Filed: Mar. 25, 2010

(65) Prior Publication Data

US 2010/0246365 A1 Sep. 30, 2010

(30) Foreign Application Priority Data

Mar. 31, 2009 (KR) .................. 10-2009-0027682

(51) Int. Cl.
*G06K 9/00* (2006.01)

(52) U.S. Cl.
USPC .......................................... 382/100; 382/254

(58) Field of Classification Search
None
See application file for complete search history.

(56) References Cited

U.S. PATENT DOCUMENTS

| | | | |
|---|---|---|---|
| 6,685,885 B2 * | 2/2004 | Nolte et al. ................. 422/64 |
| 6,937,323 B2 * | 8/2005 | Worthington et al. ........ 356/73 |
| 7,092,029 B1 * | 8/2006 | Medwick et al. ............ 348/371 |
| 7,394,593 B2 * | 7/2008 | Rottermann et al. ......... 359/388 |
| 7,548,270 B2 * | 6/2009 | Kong et al. ................. 348/366 |
| 7,567,245 B2 * | 7/2009 | Mamata ...................... 345/207 |
| 7,643,143 B2 * | 1/2010 | Fujii et al. .................. 356/336 |
| 7,725,022 B2 * | 5/2010 | Noyes et al. ................ 396/234 |
| 8,107,158 B2 * | 1/2012 | Yamazaki et al. ........... 359/292 |
| 2003/0096434 A1 | 5/2003 | Krutzik |
| 2003/0112432 A1 | 6/2003 | Yguerabide et al. |
| 2004/0253742 A1 | 12/2004 | Affleck et al. |
| 2008/0094974 A1 * | 4/2008 | Worthington ............... 369/53.2 |

FOREIGN PATENT DOCUMENTS

| | | |
|---|---|---|
| JP | H07154537 | 6/1995 |
| JP | 10-209699 | 8/1998 |
| JP | 2005300528 | 10/2005 |
| JP | 2007073107 | 3/2007 |
| JP | 2008016271 | 1/2008 |
| KR | 10-0602722 | 7/2006 |
| KR | 10-0725837 | 5/2007 |

OTHER PUBLICATIONS

European Search Report received Jul. 13, 2010 in corresponding European Application No. 10157070.3.
Office Action in corresponding Japanese Application No. 2010-072291 (3 pp.).

* cited by examiner

*Primary Examiner* — Manav Seth
(74) *Attorney, Agent, or Firm* — Staas & Halsey LLP

(57) ABSTRACT

Provided are a method and apparatus for adjusting brightness of an illumination device that is used in photographing an analysis object in a bio disk. The method includes taking images of an analysis object in a bio disk; calculating brightness of the images of the analyzing object; and adjusting brightness of an illumination device which is used in the photographing operation of the analysis object in the bio disk based on a difference between the calculated brightness and a target brightness.

12 Claims, 5 Drawing Sheets

METHOD OF ADJUSTING BRIGHTNESS OF ILLUMINATION DEVICE AND BIO DISK DRIVE USING THE METHOD

CROSS-REFERENCE TO RELATED APPLICATIONS

This application claims the benefit of Korean Patent Application No. 10-2009-0027682, filed on Mar. 31, 2009, in the Korean Intellectual Property Office, the disclosure of which is incorporated herein in its entirety by reference.

BACKGROUND

1. Field

The embodiment or embodiments relate to a bio disk drive, and more particularly, to a method for adjusting brightness of an illumination device used for taking images of a bio disk and a bio disk drive using the method.

2. Description of the Related Art

Recently developed bio disk drives take images of a bio disk in a dark environment by using an image sensor, and analyze the taken images.

Therefore, a technology for adjusting brightness of an illumination device is required in order to reduce variation in analysis results caused by a difference between brightness values of the taken images.

SUMMARY

Additional aspects and/or advantages will be set forth in part in the description which follows and, in part, will be apparent from the description, or may be learned by practice of the invention.

The embodiment provides a method of adjusting brightness of an illumination device so that brightness of images taken of a bio disk is constant.

The embodiment also provides a bio disk drive using the method of adjusting brightness.

According to an embodiment, there is provided a method of adjusting brightness of an illumination device, the method including: taking images of an analysis object in a bio disk; calculating brightness of the images of the analysis object; and adjusting brightness of an illumination device which is used in the photographing operation of the analysis object in the bio disk based on a difference between the calculated brightness and a target brightness.

The brightness of the image of the analysis object may be an average brightness of the photographed image for a predetermined time period.

The brightness of the image of the analysis object may be an average brightness of a certain region or an entire region in the photographed image.

In the adjusting of the brightness of illumination device, when the calculated brightness of the image is lower than the target brightness, a voltage or a current supplied to the illumination device may be increased, and when the calculated brightness of the image is higher than the target brightness, the voltage or the current supplied to the illumination device may be decreased.

In the adjusting of the brightness of illumination device, when the calculated brightness of the image is lower than the lowest target brightness, a voltage or a current supplied to the illumination device may be increased, and when the calculated brightness of the image is higher than the highest target brightness, the voltage or the current supplied to the illumination device may be decreased.

The method may further include capturing images of the analysis object in the bio disk after the calculated brightness reaches the target brightness after adjusting the brightness of the illumination device.

According to an aspect of the embodiment, there is provided a bio disk drive including: a bio disk having a structure for analyzing bio-materials; a camera module taking images of an analysis object in the bio disk; a controller calculating brightness of the photographed images of the analysis object, and generating an illumination control signal based on a difference between the calculated brightness and a target brightness; an illumination driver generating an illumination driving signal based on the illumination control signal; and an illumination unit generating light of an intensity which corresponds to the illumination driving signal.

The controller may calculate an average brightness of the image of the analysis object photographed by the camera module for a predetermined time period, and generate the illumination control signal based on a difference between the calculated average brightness and the target brightness.

The controller may generate the illumination control signal for increasing a voltage or a current supplied to the illumination unit when the calculated brightness is lower than the target brightness, and for decreasing the voltage or the current supplied to the illumination unit when the calculated brightness is higher than the target brightness.

The controller may generate the illumination control signal for increasing a voltage or a current supplied to the illumination unit when the calculated brightness is lower than the lowest target brightness, and for decreasing the voltage or the current supplied to the illumination unit when the calculated brightness is higher than the highest target brightness.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION OF EMBODIMENTS

Figure 1:
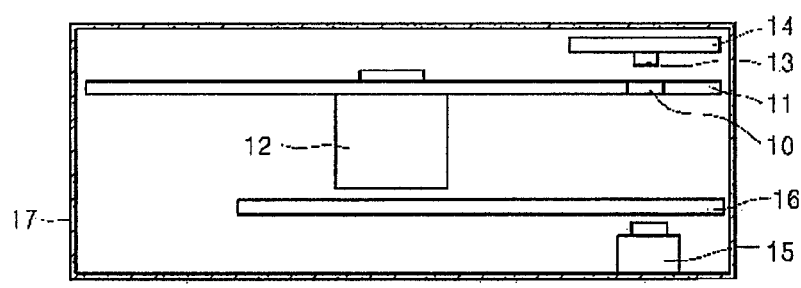
FIG. 1 is a diagram of a bio disk drive according to an embodiment.

Reference will now be made in detail to the embodiments, examples of which are illustrated in the accompanying drawings, wherein like reference numerals refer to the like elements throughout. The embodiments are described below to explain the present invention by referring to the figures.

Hereinafter, the embodiment will be described in detail by explaining embodiments with reference to the attached drawings.

After setting an intensity of light irradiated from an illumination device of a bio disk drive, brightness of images may be adjusted by using an automatic exposure function of a camera module. However, according to this method, when a tolerance range of the automatic exposure function is set too narrow, stabilization in the automatic exposure becomes too slow. On the other hand, if the tolerance range of the automatic exposure function is set too wide, the variation in the results of the analyzed images results becomes too large.

According to the embodiment, a method of adjusting brightness of an illumination device may reduce brightness variation within a tolerable range after stabilizing the automatic exposure function. The method of adjusting brightness of the illumination device according to the embodiment may be applied to a bio disk drive including a camera module which does not have an automatic exposure function.

FIG. 1 is a diagram of a bio disk drive according to an embodiment.

Referring to FIG. 1, the bio disk drive includes a bio disk 11 including an analysis object 10, a rotator 12 rotating the bio disk 11, an illumination unit 13 generating light used to take images of the analysis object 10, a printed circuit board (PCB) 14 on which the illumination unit 13 is located, a camera module 15 taking images of the analysis object 10, a PCB 16 on which the camera module 15 is located, and a case 17.

According to the embodiment, the illumination unit 13 and the camera module 15 are installed on different PCBs from each other, however, the illumination unit 13 and the camera module 15 may be installed on a single PCB.

The bio disk 11 includes various types of chambers therein. The analysis object 10 displays reaction results between reagents which are stored in the chambers to perform diagnosing operations and samples induced into the chambers through an inlet.

The illumination unit 13 generates light for taking images of the analysis object 10 in the bio disk 11. As an example, a light emission diode (LED) may be used as the illumination unit 13. Otherwise, an array including one or more LEDs may be used as the illumination unit 13. The illumination unit 13 may be installed at various locations in the bio disk drive. An intensity of light emitted from the illumination unit 13 is controlled by a method illustrated in FIG. 4 or FIG. 5.

The rotator 12 rotates the bio disk 11, and the analysis object 10 located in the bio disk 11 is photographed by the camera module 15.

Figure 2:
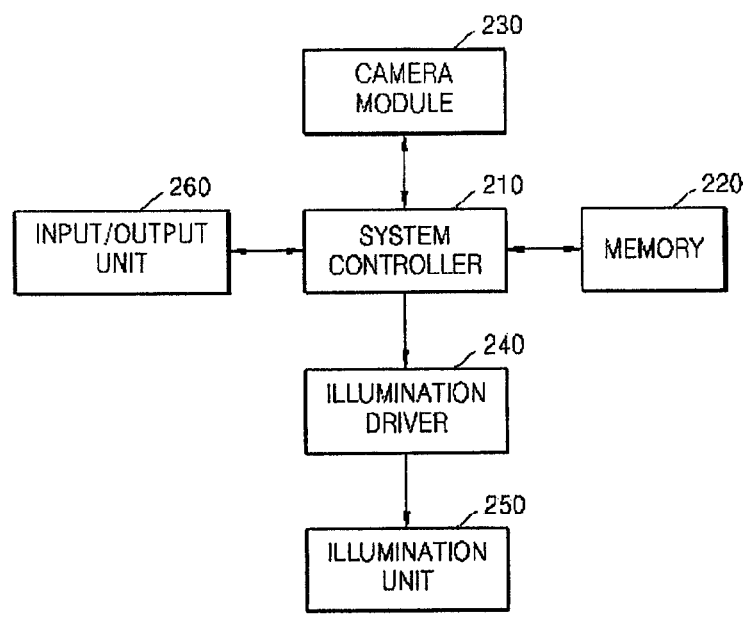
FIG. 2 is a block diagram of a circuit in the bio disk drive illustrated in FIG. 1.

Next, FIG. 2 is a block diagram of a circuit in the bio disk drive according to the embodiment.

Referring to FIG. 2, the circuit of the bio disk drive includes a system controller 210, a memory unit 220, a camera module 230, an illumination driver 240, an illumination unit 250, and an input/output unit 260.

Figure 4:
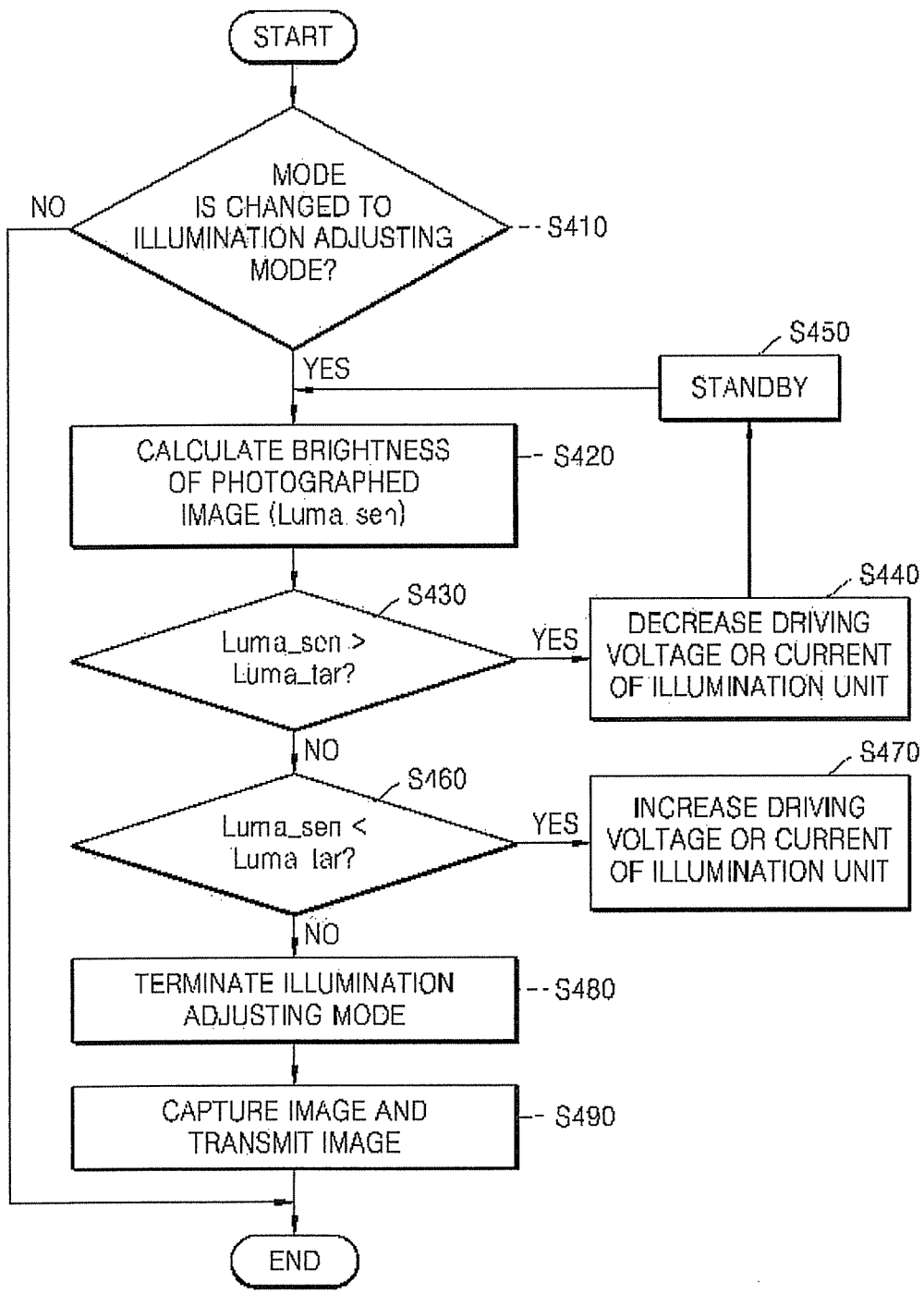
FIG. 4 is a flowchart illustrating a method of adjusting brightness of an illumination device according to an embodiment.
Figure 5:
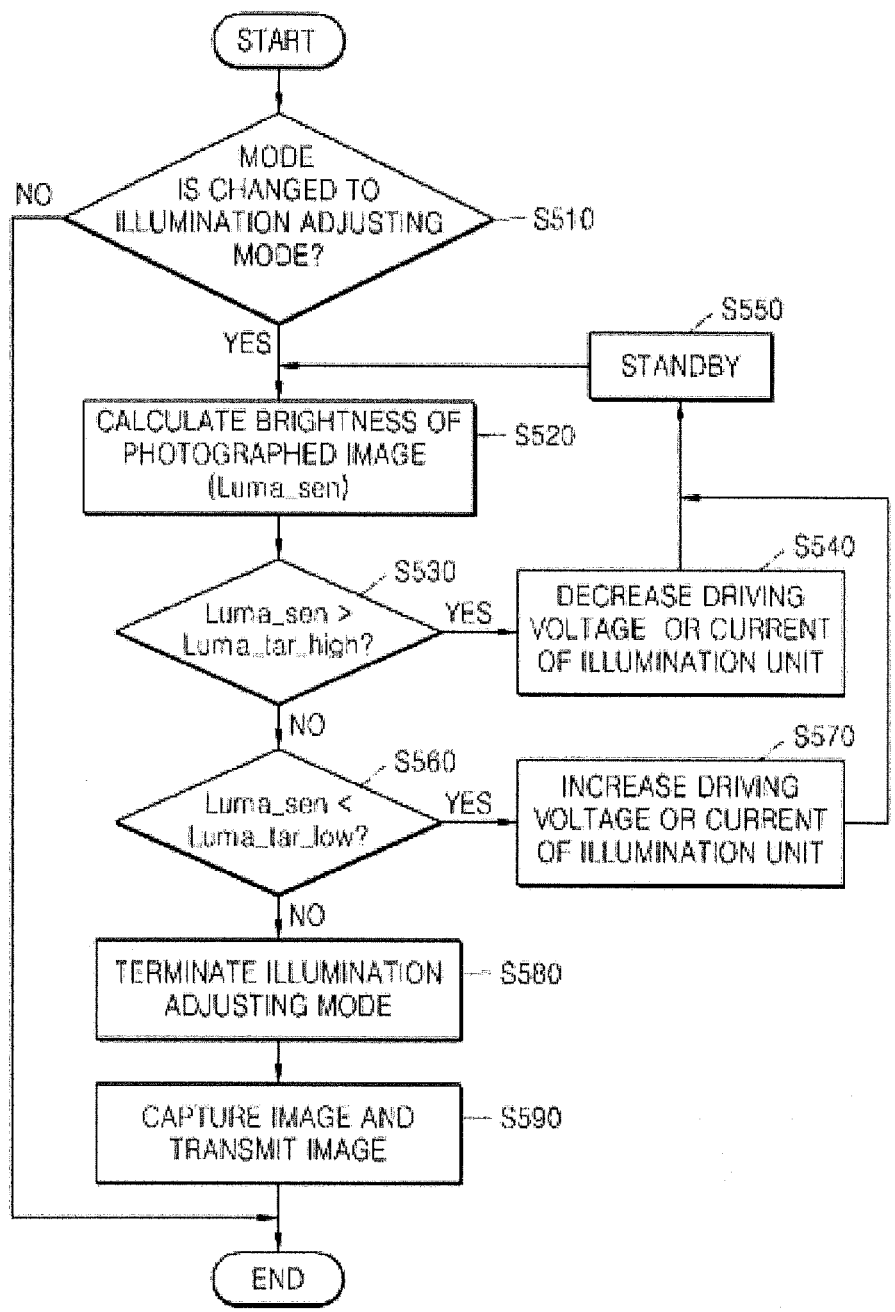
FIG. 5 is a flowchart illustrating a method of adjusting brightness of an illumination device according to another embodiment.

The system controller 210 controls the bio disk drive, and generates control signals for adjusting illumination brightness in the processes illustrated in FIGS. 4 and 5.

The memory unit 220 stores programs and data used to operate the bio disk drive, and in particular, programs and data for executing the processes illustrated in FIGS. 4 and 5.

The camera module 230 is a unit for photographing the analysis object 10 in the bio disk 11. The detailed structure of the camera module 230 is shown in FIG. 3.

Figure 3:
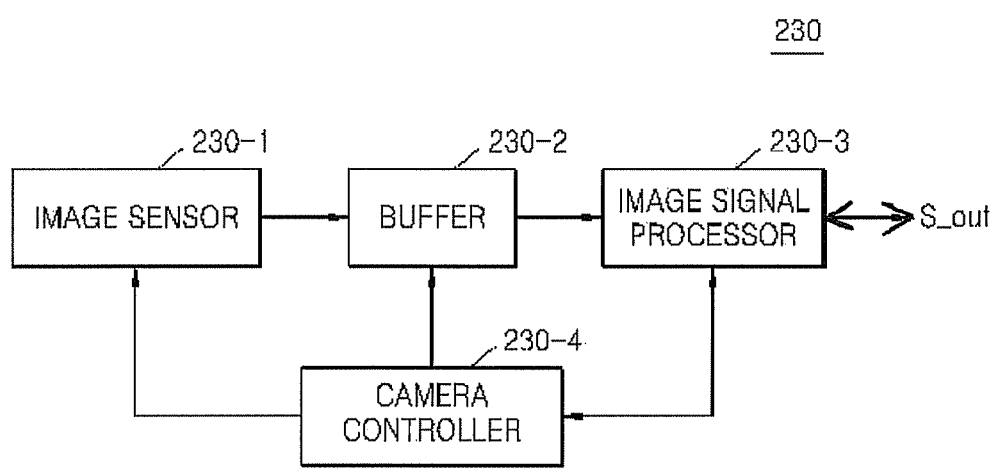
FIG. 3 is a detailed block diagram of a camera module shown in FIG. 2.

Referring to FIG. 3, the camera module 230 includes an image sensor 230-1, a buffer 230-2, an image signal processor 230-3, and a camera controller 230-4.

The image sensor 230-1 generates image data corresponding to an intensity of light reflected from the bio disk 11 or transmitting the bio disk 11. A complementary metal-oxide semiconductor (CMOS) image sensor or a charge-coupled device (CCD) image sensor may be used as the image sensor 230-1. However, the embodiment is not limited to the above examples.

The image data generated by the image sensor 230-1 according to the control signals generated by the camera controller 230-4 are temporarily stored in the buffer 230-2.

The image signal processor 230-3 processes the image data read from the buffer 230-2, and performs various correcting operations such as a gamma correction.

The camera controller 230-4 controls the elements of the camera module 230 according to the control signals transmitted from the system controller 210. In addition, the camera controller 230-4 calculates an average brightness of a certain region of the image or the entire region of the image in a predetermined time period unit in an illumination adjusting mode, and stores the calculated average brightness in an internal register. The illumination adjusting mode may be activated in an initial period of the photographing operation. However, it is not limited therein.

The above processes of calculating the average brightness of the taken image and storing the calculated average brightness may be performed by the system controller 210. The camera controller 230-4 may be integrated with the system controller 210 as a single controller.

Referring to FIG. 2, the input/output unit 260 includes an input unit generating a command for operating the bio disk drive and an output unit outputting results of processes performed in the bio disk drive according to the input command.

When electric power is supplied to the bio disk drive, the system controller 210 initializes the bio disk drive.

Then, the system controller 210 generates control signals corresponding to the commands input from the input/output unit 260. That is, when a command to start the photographing operation is input from the input/output unit 260, the system controller 210 transmits a control signal that informs the start of a photographing operation to the camera module 230. The illumination driver 240 generates an illumination driving signal which corresponds to a predetermined illumination driving voltage or a predetermined current value. Accordingly, the illumination unit 250 generates light in response to the illumination driving signal.

In addition, the camera module 230 takes an image of the analysis object 10 of the bio disk 11 by using the light generated by the illumination unit 250 according to the control signal which informs the start of the photographing operation.

The illumination adjusting mode may be set to start simultaneously with the start of the photographing operation. Otherwise, the illumination adjusting mode may be executed according to an additional illumination adjusting command generated by the input/output unit 260.

When the bio disk drive enters the illumination adjusting mode, the camera controller 230-4 or the system controller 210 executes the process of calculating the average brightness of the image photographed by the camera module 230 and storing the calculated average brightness. At this time, the average brightness of a certain region in the image or the entire region of the image may be calculated within a predetermined time period.

The system controller 210 compares the calculated brightness Luma_sen and a target brightness Luma_tar which is set initially, and generates an illumination control signal based on a difference between the calculated brightness Luma_sen and the destination brightness Luma_tar. That is, when the calculated brightness Luma_sen is lower than the target brightness Luma_tar, the system controller 210 increases the voltage or current supplied to the illumination unit 250. In addition, when the calculated brightness Luma_sen is higher than the target brightness Luma_tar, the system controller 210 generates the illumination control signal for decreasing the voltage or the current supplied to the illumination unit 250.

The illumination driver 240 generates the illumination driving signal of a voltage/current which corresponds to the illumination control signal generated by the system controller 210, and applies the generated illumination driving signal to the illumination unit 250.

The illumination unit 250 generates light of an intensity corresponding to the illumination driving signal applied from the illumination driver 240.

The system controller 210 terminates the illumination adjusting mode when the calculated brightness Luma_sen is equal to the target brightness Luma_tar during the illumination adjust mode, and then, generates a control signal for performing an image capturing process. Otherwise, the illumination adjusting mode may be terminated when the calculated brightness Luma_sen is within a target brightness range, that is, from about Luma_tar_low to about Luma_tar_high, and the control signal for performing the image capturing operation may be generated.

When the control signal for performing the image capturing operation, the camera module 230 captures the images and stores the captured images in the memory unit 220.

After that, when a request to transmit the image of the analysis object 10 is transmitted to the system controller 210 from the input/output unit 260, the system controller 210 reads the image information stored in the memory unit 220 and transmits the information to a host device (not shown) through the input/output unit 260.

Then, the host device may determine a concentration of the analysis object in the bio disk by using the transmitted image information.

If necessary, the system controller 210 may determine the concentration of the analysis object by using the image information read from the memory unit 220, and then, may transmit the determination result to the host device.

The method of adjusting brightness performed in the bio disk drive illustrated in FIG. 2 will be described with reference to the flowcharts of FIGS. 4 and 5.

FIG. 4 is a flowchart illustrating the method of adjusting brightness according to an embodiment.

The system controller 210 determines whether the bio disk drive is changed to the illumination adjusting mode (S410). The illumination adjusting mode may start simultaneously with the start of the photographing operation, or may start according to an additional illumination adjusting command generated by the input/output unit 260.

As a result of S410, when the mode of the bio disk drive is changed to the illumination adjusting mode, the brightness Luma_sen of the image photographed by the camera module 230 is calculated (S420). As an example, the brightness Luma_sen may be the average brightness of a certain region or the entire region of the image within a predetermined time period.

The system controller 210 determines whether the brightness Luma_sen of the image is higher than the target brightness Luma_tar by comparing the brightness Luma_sen which is calculated in operation S420 with the target brightness Luma_tar (S430).

Then, when the brightness Luma_sen of the image higher than the target brightness Luma_tar as a result of determination in operation S430, the system controller 210 controls the driving voltage or current that will be supplied to the illumination unit 250 to be decreased (S440). As an example, the driving voltage or current that will be supplied to the illumination unit 250 may be decreased in proportion to the difference between the brightness Luma_sen of the image and the target brightness Luma_tar, and if necessary, the driving voltage or current may be decreased.

When the brightness Luma_sen of the image is not higher than the target brightness Luma_tar as a result of determination in operation S430, the system controller 210 determines whether the brightness Luma_sen is lower than the target brightness Luma_tar (S460).

When the brightness Luma_sen is lower than the target brightness Luma_tar as a result of determination in operation S460, the system controller 210 controls the driving voltage or current that will be applied to the illumination unit 250 to be increased (S470). As an example, the driving voltage or the current that will be supplied to the illumination unit 250 may be increased in proportion to the difference between the brightness Luma_sen and the target brightness Luma_tar, or if necessary, the driving voltage or the current may be increased.

After performing the operation S440 or S470, the process is fed back to the operation S420 after waiting for a predetermined time (S450). The waiting time may be determined in consideration of the time to adjust the brightness of the illumination in response to the change in the driving voltage or the current applied to the illumination unit 250.

When the brightness Luma_sen of the image is not lower than the target brightness Luma_tar as a result of determination in operation S460, the brightness Luma_sen of the image is equal to the target brightness Luma_tar. In this case, the system controller 210 terminates the illumination adjust mode (S480).

After that, the system controller 210 captures the images photographed by the camera module 230, and transmits the captured image information to the host device through the input/output unit 260 (S490).

FIG. 5 illustrates a method of adjusting brightness according to another embodiment.

The system controller 210 determines whether a mode of the bio disk drive is changed to the illumination adjust mode (S510).

When the mode of the bio disk drive is changed to the illumination adjust mode, the brightness Luma_sen of images photographed by the camera module 230 is calculated (S520). As an example, the brightness Luma_sen of the image may be the average brightness of a certain region or entire region of the image within a predetermined time period.

The system controller 210 determines whether the brightness Luma_sen of the image is higher than the highest target brightness Luma_tar_high by comparing the brightness Luma_sen calculated in the operation S520 with the highest target brightness Luma_tar_high which is initially set (S530).

When the brightness Luma_sen of the image is higher than the highest target brightness Luma_tar_high according to the result of determination in operation S530, the system controller controls the driving voltage or the current that will be applied to the illumination unit 250 to be decreased (S540). For example, the driving voltage of the current that will be applied to the illumination unit 250 may be decreased in proportion to a difference between the brightness Luma_sen of the image and the highest target brightness Luma_tar_high, or may be decreased.

When the brightness Luma_sen of the image is not higher than the highest target brightness Luma_tar_high as a result of determination in the operation S530, the system controller 210 determines whether the brightness Luma_sen is lower than the lowest target brightness Luma_tar_low (S560).

When the brightness Luma_sen of the image is lower than the lowest target brightness Luma_tar_low as a result of determination in the operation S560, the system controller 210 controls the driving voltage or the current that will be applied to the illumination unit 250 to be increased (S570). For example, the driving voltage of the current that will be applied to the illumination unit 250 may be increased in proportion to a difference between the brightness Luma_sen of the image and the lowest target brightness Luma_tar_low, or may be increased.

After performing the operation S540 or S570, the process is fed back to the operation S520 after waiting a predetermined time (S550). Here, waiting time may be determined in consideration of the time to adjust the brightness of the illumination in response to the change in the driving voltage or the current applied to the illumination unit 250.

When the brightness Luma_sen of the image is not lower than the lowest target brightness Luma_tar_low as a result of the determination in the operation S560, it means that the brightness Luma_sen of the image is included in the target brightness range between the highest target brightness Luma_tar_high and the lowest target brightness Luma_tar_low. In this case, the system controller 210 terminates the illumination adjusting mode (S580).

After that, the system controller 210 controls the camera module 230 to capture the image and transmit the captured image information to the host device through the input/output unit 260 (S590).

The target brightness range Luma_tar_low to Luma_tar_high may be set to be narrower than a tolerable range of the target brightness in the automatic exposure function.

According to the method of adjusting illumination brightness illustrated in FIG. 4, the illumination brightness for performing the photographing operation of the analysis object in the bio disk drive coincides exactly with the target brightness Luma_tar. On the other hand, according to the method of adjusting illumination brightness illustrated in FIG. 5, the illumination brightness for performing the photographing operation of the analysis object in the bio disk drive may be included in the target brightness range Luma_tar_low to Luma_tar_high. Brightness may be adjusted more precisely by using the method illustrated in FIG. 4 than that of FIG. 5, however, the time for adjusting brightness when the method illustrated in FIG. 4 is used may be longer than that when the method illustrated in FIG. 5 is used.

The method illustrated in FIG. 4 or the method illustrated in FIG. 5 may be selected according to a type of a method of analyzing images of the analyzing object in the bio disk drive.

The embodiment may be applied to a camera module having an automatic exposure function in a bio disk drive, or may be applied to a camera module that does not have an automatic exposure function.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A method of adjusting brightness of an illumination device, the method comprising:
    taking images of an analysis object in a bio disk;
    calculating brightness of the images of the analysis object; and
    adjusting brightness of an illumination device which is used in the photographing operation of the analysis object in the bio disk based on a difference between the calculated brightness and a predetermined target brightness,
    wherein in the adjusting of the brightness of illumination device, when the calculated brightness of the image is lower than the lowest target brightness, a voltage or a current supplied to the illumination device is increased, and when the calculated brightness of the image is higher than the highest target brightness, the voltage or the current supplied to the illumination device is decreased.

2. The method of claim 1, wherein the brightness of the image of the analysis object is an average brightness of a certain region or an entire region in the photographed image.

3. The method of claim 1, wherein in the adjusting of the brightness of illumination device, when the calculated brightness of the image is lower than the target brightness, a voltage or a current supplied to the illumination device is increased, and when the calculated brightness of the image is higher than the target brightness, the voltage or the current supplied to the illumination device is decreased.

4. The method of claim 1, further comprising capturing images of the analysis object in the bio disk after the calculated brightness reaches the target brightness after adjusting the brightness of the illumination device.

5. A bio disk drive comprising:
    a bio disk having a structure to analyze bio-materials;
    a camera module to take images of an analysis object in the bio disk;
    a controller to calculate brightness of the photographed images of the analysis object, and to generate an illumination control signal based on a difference between the calculated brightness and a predetermined target brightness;
    an illumination driver to generate an illumination driving signal based on the illumination control signal; and
    an illumination unit to generate light of an intensity which corresponds to the illumination driving signal, wherein the controller generates the illumination control signal for increasing a voltage or a current supplied to the illumination unit when the calculated brightness is lower than the lowest target brightness, and for decreasing the voltage or the current supplied to the illumination unit when the calculated brightness is higher than the highest target brightness.

6. The bio disk drive of claim 5, wherein the controller calculates an average brightness of the image of the analysis object photographed by the camera module for a predetermined time period, and generates the illumination control signal based on a difference between the calculated average brightness and the target brightness.

7. The bio disk drive of claim 5, wherein the controller generates the illumination control signal for increasing a voltage or a current supplied to the illumination unit when the calculated brightness is lower than the target brightness, and for decreasing the voltage or the current supplied to the illumination unit when the calculated brightness is higher than the target brightness.

8. The bio disk drive of claim 5, further comprises a memory to store programs and/or data to operate the bio disk drive.

9. The bio disk drive of claim 5, wherein the illumination unit comprises a light emit diode (LED).

10. The bio disk drive of claim 5, wherein the camera module comprises:
    an image sensor to generate an image data;
    a camera controller to control the camera module; and
    an image signal processor to process the image data.

11. The bio disk drive of claim 10, the camera module further comprises a buffer to temporarily store the image data.

12. The method of claim 1, wherein the brightness of the image of the analysis object is an average brightness of the photographed image for a predetermined time period.

* * * * *